United States Patent [19]

Askanazi

[11] Patent Number: 5,017,616

[45] Date of Patent: May 21, 1991

[54] METHOD FOR IMPROVING VENTILATION DURING SLEEP AND TREATING SLEEP RELATED VENTILATION ABNORMALITIES

[76] Inventor: Jeffrey Askanazi, 25 Pine St., Haworth, N.J. 07641

[21] Appl. No.: 443,765

[22] Filed: Nov. 30, 1989

[51] Int. Cl.$^5$ .............................................. A61K 31/195
[52] U.S. Cl. .................................................... 514/561
[58] Field of Search ................................ 514/561, 923

[56] References Cited

U.S. PATENT DOCUMENTS 4,209,531  6/1980  Berry .................................... 514/561

FOREIGN PATENT DOCUMENTS 2037161  7/1980  United Kingdom .

Primary Examiner—Stanley J. Friedman
Assistant Examiner—Raymond J. Henley, III

[57] ABSTRACT

A method for improving ventilation during sleep and treating sleep-related ventilation abnormalities. To this end, the present invention provides a method of using branched-chain amino acids as an effective therapy for sleep apnea. The branched-chain amino acid composition can be administered either parenterally or enterally, and can be administered alone or in combination with other nutrients. The branched-chain amino acid composition of the present invention functions as a ventilatory stimulator during sleep and does not result in any adverse effects either to the patient or to the sleep patterns of the patient. Preferably, the branched-chain amino acids comprise 60 to 85% of an amino acid solution that is administered to the patient.

16 Claims, No Drawings

METHOD FOR IMPROVING VENTILATION DURING SLEEP AND TREATING SLEEP RELATED VENTILATION ABNORMALITIES

BACKGROUND OF THE INVENTION

The present invention relates to a method for the use of branched-chain amino acids to improve ventilation during sleep. More specifically, the present invention relates to a method for treating sleep related ventilation problems, such as apnea.

Sleep apnea is recognized as a serious and often life threatening abnormality of the breathing pattern. See, Kales, et al, *Sleep Disorders: Sleep Apneas and Narcolepsy*, Ann. Intern. Med., 106:434–443, 1987. The morbidity of sleep apnea is due to a decrease oxygenation of the arterial blood and carbon dioxide retention secondarily to alveolar hypoventilation.

The condition of sleep apnea has been defined as the cessation of breathing for at least 10 seconds, that occurs at least 30 times during a 7 hour period of sleep. This definition, however, is based on sleep laboratory studies and accordingly, is not clinically applicable. Instead, arterial oxygen desaturation during sleep is the critical factor in determining sleep apnea. See, Block, et al, *Sleep Apnea, Hypopnea and Oxygen Desaturation in Normal Subjects*, New England Journal of Medicine, 300:513–517, 1979.

The sleep apnea syndrome has been observed as a primary disease in otherwise healthy subjects. Apneas can be divided into three sub-groups: central; obstructive; and mixed. Abnormal respiratory control is believed to be involved in all types of sleep apneas. Apneic breathing patterns during sleep occur also in association with certain other conditions, such as: morbid obesity; coronary disease; and congestive heart failure. See, Walse, et al, *Upper Airway Obstruction in Obese Patients With Sleep Disturbances and Somnolence*, Ann. Intern. Med. 76: 185–192, 1972; DeOlazabal, et al, *Disordered Breathing and Hypoxia During Sleep in Coronary Artery Disease*, Chest, 82:548–552, 1982; and Dark, et al, *Breathing Pattern Abnormalities and Arterial Desaturation During Sleep in the Congestive Heart Failure Syndrome, Improvement Following Medical Therapy*, Chest, 91:833–836, 1987. Patients recovering from anesthesia also frequently exhibit apneic breathing patterns.

Most patients with sleep apnea snore heavily and many exhibit severe oxygen desaturation. Oxygen desaturation during sleep may be associated with pulmonary and systematic hypertension and cardiac arrhythmias. Tilkian, et al, Sleep-Induced Apnea Syndrome, *Prevelance of Cardiac Arrhythmias and Their Reversal After Tracheostomy*. Am.J.Med. 63(3):348–358, 1976; and Tilkian, et al, *Hemodynamics in Sleep-Induced Apnea*, Am. Intern. Med. 85(6):714–719, 1977.

The typical management of sleep apnea syndrome is to relieve upper air obstruction and to also stimulate respiratory activity. Typically, pharmacologic techniques are utilized to achieve these goals. However, drug therapy alone is not usually effective in relieving sleep apneas. Moreover, such drug therapies are often associated with adverse side effects.

One drug that is used is Medroxyprogesterone acetate (MPA). MPA has been found to be a moderate, sustained ventilatory stimulant in man. MPA reduces sleep apnea in less than half of all patients. Strohl, et al, *Progesterone Administration and Progressive Sleep Apneas*, J. A. M. A., 245:1230–1232, 1981. But, MPA causes impotence in men and therefore the desirability and use of this drug is limited.

Another drug, protiptyline has been found to improve sleep apnea in some patients. This drug, however, is associated with such serious side effects such as: constipation; urinary retention; ataxia; and confusion. Brownell, et al, *Protiptyline in Obstructive Sleep Apnea*, New England Journal of Medicine, 307:1037–1042, 1982.

Accordingly, although pharmacologic interventions can be, in some cases, effective in decreasing the frequency and duration of sleep apneas, and the extent of oxygen desaturation in patients, the usefulness of such drug therapy is limited due to the adverse side effects of such drugs. Therefore, there is a need for an improved therapy for treating patients with sleep apnea.

SUMMARY OF THE INVENTION

The present invention provides a method for improving ventilation during sleep. To this end, the present invention provides a method of using branched-chain amino acids as an effective therapy for sleep apnea. The branched-chain amino acid composition can be administered either parenterally or enterally, and can be administered alone or in combination with other nutrients. The branched-chain amino acid composition of the present invention functions as a ventilatory stimulator during sleep and does not result in any adverse effects either to the patient or to the sleep patterns of the patient.

Preferably, the branched-chain amino acids comprise 60 to 85% of an amino acid solution that is administered to the patient.

In an embodiment of the present invention, the composition comprises, per 100 ml, approximately 1.30 grams of Isoleucine, 1.38 grams of Leucine, and 1.24 grams of Valine.

In an embodiment of the method of the present invention, approximately 4 grams of branched-chain amino acids are administered per hour.

Additional features and advantages of the present invention are described in, and will be apparent from, the detailed description of the presently preferred embodiments.

DETAILED DESCRIPTION OF THE PRESENTLY PREFERRED EMBODIMENTS

Branched-chain amino acid infusions have been shown to increase ventilatory drive when compared to conventional amino acid solutions and 5% dextrose. The infusion of amino acids increases ventilation by shifting the response curve of minute ventilation to arterial carbon dioxide tension to the left during carbon dioxide inhalation.

The inventor of the present invention has found that by altering an amino acid composition, by increasing the amount of branched-chain amino acids, an increase in ventilation and a decrease in arterial carbon dioxide tension is achieved. Branched-chain amino acids induce a larger decrease in arterial carbon dioxide tension and a larger increase in ventilatory response to carbon dioxide than a conventional amino acid solution. It has been found that branched-chain amino acids will induce a larger decrease in arterial carbon dioxide tension and a larger increase in ventilatory response to carbon dioxide than a conventional amino acid solution when infused for four hours after an overnight fast. This affect is even more dramatic when the infusion is continued over a 48 hour period.

By way of example, and not limitation, examples of the present invention will now be set forth.

EXAMPLES

Example No. 1

Five non-smoking healthy male volunteers (24 to 32 years of age), with no sleep disorders and who were not taking any medication, were studied. The subjects were studied on three separate nights. One night was a control that did not include the infusion of any solution and on the other two nights a continuous infusion of either BCAA (3.5% solution of 100% BCAA) or placebo (½ normal saline) was administered. The composition of the BCAA solution used was as follows:

| Composition Of BCAA Solution (per 100 ml) | |
|---|---|
| Isoleucine | 1.38 g |
| Leucine | 1.38 g |
| Valine | 1.24 g |
| Total nitrogen | 443 mg |

The BCAAs/saline solutions were infused in a single blind crossover design with infusion/control nights randomly assigned within every patient. The patients were allowed no food intake after 5 pm and no stimulants (i.e., coffee) were allowed after 12 noon on the study days.

The subjects were admitted at 8:30 p.m. to a sleep-awake center. On the nights they were to receive an infusion, a peripheral cannula was inserted into the patients for the infusion. Sleep stages were studied using a 12-channel polysomnographic monitor (Grass P78). Chest wall movements were measured with a pneumograph consisting of a small circular rubber bellows attached around the chest. The bellows were connected to a volumetric pressure transducer. The signals were amplified with a DC amplifier. Air flow at the mouth and nose was measured by a thermistor placed at each nostril and the upper lip in the midline position. An ear oximeter (Ohmeda Biox 3700) was used to record oxyhemoglobin saturation. End tidal $CO_2$ was measured using a capnograph (Normocap, Datex, Finland), the sampling tube was placed in the nasopharynx. A continuous electrocardiogram ran during the night.

The infusion solutions were started one hour prior to the estimated bedtime. The infusion rate was 100 ml/hour and infusion was discontinued in the morning at 7:30 a.m. The BCAA dose was 4 grams of amino acids/hour responding 0.443 grams of nitrogen/hour.

The end-tidal $CO_2$ levels during nights of BCAA infusion (44±5 mmHg) were lower than during control nights (C: 52±1 mmHg, $p<0.01$ and S: 50±3 mmHg, $p<0.05$). There was a trend ($p<0.2$) of increase in $O_2$-saturation levels. The results are set forth in Table 1 below:

TABLE 1

The highest end-tidal $CO_2$ (ETCO$_2$), and lowest SaO$_2$ values during the study nights; C (control nights without infusion), BCAA and NaCl

| | C | BCAA | NaCl |
|---|---|---|---|
| ETCO$_2$ (mmHg) | 52 ± 1.4 | 44 ± 5.3 | 50 ± 2.6 |
| SaO$_2$ (%) | 93 ± 1.6 | 95 ± 2.3 | 94 ± 0.5 |

There was no significant change in the amount of REM sleep. The amount of stage 3 sleep and the combined stage 3 & 4 sleep were greater during BCAA nights than control nights (7.2±4.0% vs 4.3±2.8%, <0.05 and 15.9 ±3.0% vs. 12.3±3.9%, p<0.02, respectively). Sleep efficiency was slightly, but not significantly, decreased with either infusion (BCAA:87±8, Nacl:87±8, and C:92±10). One patient had 10 apneic episodes on the control night, 5 with NaCl, but none with BCAA infusion. The polysomnographic data is summarized in Table 2 below:

TABLE 2

The polysomnograph data from the three study nights

| | C | BCAA | NaCl |
|---|---|---|---|
| Sleep efficiency | 92 ± 10 | 87 ± 8 | 87 ± 8 |
| Sleep latency | 2.1 ± 3.2 | 4.7 ± 4.9 | 2.1 ± 1.5 |
| Stage 1 sleep | 3.2 ± 2.3 | 5.3 ± 5 | 4.5 ± 1.8 |
| Stage 2 sleep | 59 ± 3.7 | 59 ± 3.2 | 62 ± 5.5 |
| Stage 3 sleep | 4.3 ± 2.8 | 7.2 ± 4 | 9 ± 6 |
| Stage 4 sleep | 8 ± 6 | 7 ± 3 | 6 ± 5 |
| Stage 3 & 4 | 12 ± 4 | 16 ± 3 | 15 ± 9 |
| REM sleep | 25 ± 6 | 20 ± 5 | 19 ± 4 |
| REM latency | 80 ± 36 | 95 ± 109 | 73 ± 17 |
| Apneas | 2.5 ± 5 | 0 ± 0 | 1.3 ± 2.5 |
| Hypopneas | 7 ± 11 | 4 ± 6 | 4 ± 6 |

All subjects had slightly hypercapnic highest end-tidal $CO_2$ values during both control nights and BCAA infusion decreased it to eucapnic levels (range 44–36 mmHg). BCAA infusions did not cause hypocapnia and thus the risks of causing hyperventilation and respiratory alkalosis appears negligible. There was not a significant change in oxygen SaO$_2$ during BCAA infusion, which was to be expected as all patients were in good health and had normal saturation levels (range for lowest value was 93–99%). One subject had apneas during control nights but not during BCAA infusion. Although some investigators have indicated that the hypoxic ventilatory drive is more important in sleep apnea patients than hypercapnic ventilatory drive, the results indicate enhancing the respiratory drive by BCAA infusion assists in normalizing the breathing patterns during sleep in healthy subjects.

The sleep patterns, even with the infusion of BCAAs, remained largely intact. There was no significant change in the amount of REM sleep or REM latency. The amount of stage 3 sleep and combined stage 3 and 4 sleep increased significantly during BCAA nights when compared to control night without infusion. The study demonstrates that BCAA infusions indeed affect neurophysiological functions during sleep. The accentuation of the respiratory effects of amino acids by BCAA can have important clinical relevance for patients with decreased ventilatory drive due to anesthesia, medication, prolonged administration of 5% dextrose, or sleep apneas due to different origins.

Example No. 2

A 31 year old, morbidly obese white female was admitted with a diagnosis of increasing shortness of breath, peripheral cyanosis secondary to morbid obesity with a history of sleep disturbance (diagnosis: sleep apnea versus obesity hypoventilation). The patient had been previously maintained on home oxygen therapy and nasal CPAP. The patient presented increasing dyspnea on exertion of a half a block, four to five pillow orthopnea, frequent night awakenings, and chronic peripheral edema. The patient also had perioral and peripheral cyanosis, complained of feeling very tired in the mornings, and had a history of lightheadedness and diffuse constant chronic numbness in the morning.

During admission, the patient's blood gases were measured. The blood gases were arterial P02 67 mmHg, arterial PC02 50 mmHg and PH 7.34. Vital capacity was 1.1 liter (predicted 3.8), forced expiratory volume .81 liter (predicted 2.7).

A past medical history was taken and was significant in that a gastric stapling performed at St. Luke's eight years prior, had became "unbuttoned."

The medicines the patient was given, at the time of admission included Lasix and Aminophylin. The patient was also started on a 600 calorie diet. The patient's blood gases were: arterial P02 46, arterial PC02 51, PH 7.42 while awake.

The patient began a regimen of branched chain amino acid parenteral nutrition. The patient was started on a Branchamine infusion of 4%, available from Clintec Nutrition, Deerfield, Illinois, at 100 ml/hr in the hospital. This was well tolerated. After the patient left the hospital, home infusions were instituted on a nightly basis at a rate of 100 ml/hr of 4% Branchamine, available from Clintec Nutrition. Soon thereafter, symptomatic improvement occurred.

Following nine months of these infusions, the patient remained stable at home, was more energetic upon awakening, and many of her morning symptoms had resolved completely. The patient's vital capacity had increased to 1.17 1 and her FEVI had increased to 0181 1/sec. Feelings of lightheadedness and other symptoms previously reported had improved as did the perioral and peripheral cyanosis the patient had experienced upon awakening.

The increase in vital capacity and FEVI demonstrates that the Branchamine has improved the patient's sleep apnea.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method of treating sleep-related ventilation abnormalities comprising:
administering to a patient in need thereof a therapeutically effective amount of an amino acid solution comprising therapeutically effective amounts of the branched-chain amino acids isoleucine, leucine, and valine.

2. The method of claim 1 wherein the solution is administered parenterally.

3. The method of claim 1 wherein the solution is administered enterally.

4. The method of claim 1 wherein approximately 4 grams of branched-chain amino acids are administered per hour.

5. A method of treating sleep apnea comprising:
administering to a patient in need thereof a solution comprising approximately 60 to about 85% branched-chain amino acids isoleucine, leucine, and valine.

6. The method of claim 5 wherein the solution is administered parenterally.

7. The method of claim 5 wherein the solution is administered enterally.

8. The method of claim 5 including the step of administering approximately 0.443 grams of total nitrogen per hour.

9. The method of claim 5 wherein approximately 4 grams of branched-chain amino acids are administered per hour.

10. A method of treating sleep apnea comprising administering to a patient in need thereof a composition comprising per 100 ml: approximately 1.38 grams of Isoleucine; approximately 1.38 grams of Leucine; and approximately 1.24 grams of Valine.

11. The method of claim 10 wherein approximately 100 ml of composition are administered per hour to the patient.

12. The method of claim 10 wherein the grams of total nitrogen is approximately 0.443.

13. The method of claim 10 wherein the solution is administered parenterally.

14. The method of claim 10 wherein the solution is administered enterally.

15. The method of claim 1 wherein the solution comprises approximately 60 to 85% branched-chain amino acids.

16. The method of claim 5 wherein the solution comprises approximately 100% branched-chain amino acids.

* * * * *

UNITED STATES PATENT AND TRADEMARK OFFICE
CERTIFICATE OF CORRECTION

PATENT NO. : 5,017,616

DATED : May 21, 1991

INVENTOR(S) : Askanazi et al

It is certified that error appears in the above—identified patent and that said Letters Patent is hereby corrected as shown below:

Title Page, items [19] and [76]:

Please correct the cover page listing the inventor as "Askanazi" to read --Askanazi et al--.

Please correct the cover page to read --Inventors:-- instead of "Inventor:".

Please also correct the cover page to list:

--Susan Trimbo
  737 Ridge Ave. #3
  Evanston, IL 60202-- as the second inventor.

Signed and Sealed this

Fifth Day of January, 1993

Attest:

DOUGLAS B. COMER

*Attesting Officer*   Acting Commissioner of Patents and Trademarks